United States Patent [19]
Wong et al.

[11] Patent Number: 5,565,188
[45] Date of Patent: Oct. 15, 1996

[54] POLYALKYLENE BLOCK COPOLYMERS AS SURFACE MODIFIERS FOR NANOPARTICLES

[75] Inventors: Sui-Ming Wong, Collegeville; Eugene R. Cooper, Berwyn; Shugian Xu, Exton, all of Pa.

[73] Assignee: NanoSystems L.L.C., Collegeville, Pa.

[21] Appl. No.: 393,972

[22] Filed: Feb. 24, 1995

[51] Int. Cl.$^6$ ............................................. A61K 9/14
[52] U.S. Cl. ................ 424/9.411; 424/9.4; 424/9.45; 424/489; 424/495; 424/499; 514/718; 514/975
[58] Field of Search ...................... 424/489, 495, 424/499, 4, 5; 514/718, 975

[56] References Cited

U.S. PATENT DOCUMENTS

| | | | |
|---|---|---|---|
| 4,587,365 | 5/1986 | Anchor | 568/619 |
| 5,041,346 | 8/1991 | Giles | 429/192 |
| 5,145,684 | 9/1992 | Liversidge et al. | 424/489 |
| 5,326,552 | 6/1994 | Na et al. | 424/4 |

OTHER PUBLICATIONS

Chemical Abstracts 117:151640, "High Molecular Weight Polyetherpolyols".

*Primary Examiner*—Frederick Krass
*Attorney, Agent, or Firm*—Rudman & Balogh

[57] ABSTRACT

There is disclosed a composition containing nanoparticles having a surface modifier wherein the surface modifier is a block copolymer containing one or more polyoxyethylene blocks and one or more polyoxy(higher alkylene) blocks wherein at least some of the blocks are linked together by a linking group characterized in that the linking group is an oxymethylene group.

6 Claims, No Drawings

POLYALKYLENE BLOCK COPOLYMERS AS SURFACE MODIFIERS FOR NANOPARTICLES

FIELD OF THE INVENTION

The present invention is directed to nanoparticles having, as a surface modifier, a polyalkylene block copolymer.

BACKGROUND OF INVENTION

Bioavailability is the degree to which a therapeutic agent becomes available to the target tissue after administration. Many factors can affect bioavailability including the dosage form and various properties, e.g., dissolution rate of the therapeutic agent. Poor bioavailability is a significant problem encountered in the development of pharmaceutical compositions, particularly those containing an active ingredient that is poorly soluble in water. Poorly water soluble therapeutic agents, i.e., those having a solubility less than about 10 mg/ml, tend to be eliminated from the gastrointestinal tract before being absorbed into the circulation. Moreover, poorly water soluble therapeutic agents tend to be unsafe for intravenous administration techniques, which are used primarily in conjunction with fully soluble therapeutic or diagnostic agents.

Nanoparticles, described in U.S. Pat. No. 5,145,684, are particles consisting of a poorly soluble therapeutic or diagnostic agent onto which are adsorbed a non-crosslinked surface modifier, and which have an average particle size of less than about 400 nanometers (nm). These nanoparticles provide for increased bioavailability and for imporved diagnostic charactistics compared to other materials having larger sizes.

In U.S. Pat. No. 4,534,959, there is described a composition in an aersol container. When sprayed the composition gels on the surface of living tissue. This composition contains a polyoxyethylene-polyoxypropylene copolymer. However the copolymer must be present in high percentage. Further, the therapeutic agent must be solubilized. U.S. Pat. No. 3,867,533 relates to another aqueous gel composition; U.S. Pat. No. 4,465,663 is similar and relates to cosmetic gels.

A wide variety of surface modifiers are described in the '684 patent and in subsequent patents and applications that relate to nanoparticles as described therein. However, there is a continuing need for surface modifiers that have rehological properties that make them particularly advantageous for a variety of uses.

SUMMARY OF THE INVENTION

In accordance with the present invention there is provided a composition comprised of nanoparticles comprising a therapeutic or dianostic agent having a surface modifier adsorbed on the surface thereof, the improvement wherein the surface modifier is a block copolymer containing one or more polyoxyethylene blocks and one or more polyoxy(higher alkylene) blocks wherein at least some of the blocks are linked together by a linking group characterised in that the linking group is an oxymethylene group.

In accordance with a preferred embodiment, the nanoparticles include a therapeutic or diagnostic agent.

DESCRIPTION OF PREFERRED EMBODIMENTS

The surface modifier adsorbed to the surface of the nanoparticles of the invention is a block copolymer containing one or more polyoxyethylene blocks and one or more polyoxy(higher alkylene) blocks wherein at least some of the blocks are linked together by a linking group characterised in that the linking group is an oxymethylene group.

Preferred copolymers of the invention include those wherein the polyoxy(higher alkylene) blocks are selected from polyoxypropylene and polyoxybutylene blocks.

In one embodiment, block copolymers are provided having the following repeating units in random order

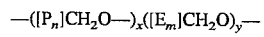

wherein

P is oxypropylene;

E is oxyethylene;

n is an integer from 2 to 70, preferably from 4 to 20;

m is an integer from 2 to 250, preferably from 9 to 20;

x is an integer from 1 to 100, preferably from 1 to 10; and, y is an integer from 1 to 100, preferably from 1 to 50.

In a particularly preferred embodiment block copolymers are used having the following repeating units in random order:

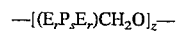

wherein

P is oxypropylene;

E is oxyethylene;

r is an integer from 2 to 160, preferably from 75 to 150;

s is an integer from 15 to 65, preferably from 30 to 50; and, z is an integer from 2 to 50, preferably from 2 to 10.

The molecular weight of a block copolymer as measured by gel permeation chromatography against poly(oxyethylene) standards may range from 10,000 to 500,000, preferably from 50,000 to 250,000.

The polymers can be prepared by a process wherein one or more dihydroxy terminated polymers selected from poly(ethylene glycol), poly(higher alkylene glycol) and block copolymers thereof are reacted in solution with a dihalomethane in the presence of a base.

Examples of suitable solvents in which the reagents can be dissolved include dihalomethanes and other known organic solvents such as benzene, chlorobenzene and toluene or mixtures thereof.

Preferably, an excess of the dihalomethane reagent is used as the solvent. Even though the dihalomethane is used in an amount which can far exceed the stoichiometric amount needed to couple with the polymeric reactants, products of high molecular weight can still be achieved.

Although any dihalomethane or mixture thereof may be used such as dichloromethane, dibromomethane or diiodomethane, the preferred dihalomethane is dichloromethane.

The required alkaline reaction conditions may be obtained by incorporating one or more bases such as sodium hydroxide and potassium hydroxide.

Examples of the dihydroxy terminated polymer starting materials include the polyethylene glycols (PEGs) and the polypropylene glycols (PPGs) which are available commercially. Specific examples include PEG 400, PEG 6000 and PPG 1000 for which the number associated with the name "PEG" or "PPG" indicates the average molecular weight of the polymer and is proportional to the average number of repeating oxyethylene or oxypropylene units in the polymer. Preferred polyalkylene glycols have molecular weights ranging from 200 to 10,000 and particularly PEG 6000.

Further examples of the dihydroxy terminated polymer starting materials include the dihydroxy terminated E—P—E triblock copolymers of poly(oxyethylene) (E) and poly(oxypropylene) (P) which are commercially available in the form of Pluronic™ surfactants. These starting materials provide the "$(E_rP_sE_r)$" portion of the block copolymers defined above. Preferred triblock copolymers have molecular weights ranging from 4,000 to 15,000. Particular Pluoronic™ surfactants that can be used as starting materials include F108, F68, F127 and L6000 and particularly F108. Triblock copolymers derived from F108, which has longer chain lengths of propyleneoxy groups, provide better hydrophobic interactions with the therapeutic or diagnositc agent particles. This povides better size reduction of particles. Further, F108 has a gel point very close to physiological temperature at low concentrations. F108 corresponds to the "$(E_rP_sE_r)$" portion r is 141 and s is 44.

The copolymers contain both hydrophilic polyoxyethylene blocks and hydrophobic polyoxy(higher alkylene) blocks. The balance between the hydrophilicity and hydrophobicity of the copolymers can be adjusted by appropriate choice of starting materials to give the optimum physical and chemical characteristics required.

The currently preferred block copolymer has the formula:

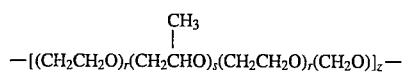

wherein r is 141; s is 44 and z is 3 to 4.

The block copolymers that are useful in the present invention have desirable rehological properties for use in therapeutic and diagnostic compositions. At concentrations as low as 2.5% w/v in phosphate balance salt solution (PBS) or in water, particular examples of the described block copolymers have gel points close to physiological temperature (37.4° C.). The viscosity of these block copolymers at 3.5% and 5.5% in PBS change abruptly from less than 20 cps at room temperature to more than 1500 cps at physiological temperature while the pH and osmolality of the block copolymer solutions remain comparable to PBS. Thus, compositions containing these block copolymers can be administered (e.g. subcutaniously or orally) as low viscosity compositions at room temperature and, when they reach physiological temperature, will tend to gel.

Because of these and other properties, the described block copolymers are useful as bioadhesives and/or control release agents for the delivery of therapeutic or diagnostic agents to the eye, ear, pulmonary systems, biocavity and gastrointestinal tract.

Therapeutic or Diagnostic Agents

The present surface modifiers are particularly useful with therapeutic agents for the treatment of the eye, particularly therapeutic agents for treatment of glaucoma, such as Betoptic™ available from Alcon Laboratories (betaxolol hydrochloride; Cortisporin™ available from Burroughs Wellcome (polymyxin B sulfate). The currently preferred therapeutic agent is Timoptic™, available from Merck & Co. Its chemical name is:
(S)-1-[(1,1-dimethyl-ethyl)amino]-3-[[4-(4-morpholinyl)-1,2,5-thiadiazol-3-yl-oxy]-2-propanol (Z)butenedioate (1:1) salt.

The particles can comprise a wide variety of other therapeutic or diagnostic agents. (Therapeutic agents are sometimes referred to as drugs or pharmaceuticals. The diagnostic agent referred to is typically a contrast agent such as an x-ray contrast agent but can also be other diagnostic materials.) The therapeutic or diagnostic agent exists as a discrete, crystalline phase. The crystalline phase differs from a non-crystalline or amorphous phase which results from precipitation techniques, such as described in EPO 275,796.

The invention can be practiced with a wide variety of therapeutic or diagnostic agents. The therapeutic or diagnostic agent preferably is present in an essentially pure form. The therapeutic or diagnostic agent must be poorly soluble and dispersible in at least one liquid medium. By "poorly soluble" it is meant that the therapeutic or diagnostic agent has a solubility in the liquid dispersion medium of less than about 10 mg/ml, and preferably of less than about 1 mg/ml. A preferred liquid dispersion medium is water. However, the invention can be practiced with other liquid media in which a therapeutic or diagnostic agent is poorly soluble and dispersible including, for example, aqueous salt solutions, safflower oil and solvents such as ethanol, t-butanol, hexane and glycol. The pH of the aqueous dispersion media can be adjusted by techniques known in the art.

Suitable therapeutic or diagnostic agents can be selected from a variety of known classes of therapeutic or diagnostic agents including, for example, analgesics, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immuriological agents, lipid regulating agents, muscle relaxants, parasympathomimetics, parathyroid calcitonin and biphosphonates, prostaglandins, radio- pharmaceuticals, sex hormones (including steroids), anti-allergic agents, stimulants and anoretics, sympathomimetics, thyroid agents, vasodilators and xanthines. Preferred therapeutic or diagnostic agents include those intended for oral administration and intravenous administration. A description of these classes of therapeutic agentsand diagnostic agents and a listing of species within each class can be found in Martindale, The Extra Pharmacopoeia, Twenty-ninth Edition, The Pharmaceutical Press, London, 1989. The therapeutic or diagnostic agents are commercially available and/or can be prepared by techniques known in the art.

Representative illustrative species of therapeutic or diagnostic agents include:

5α, 17α,-1'-(methylsulfonyl)-1'H-pregn-20-yno[3,2-c]-pyrazol-17-ol (Danazol);

Steroid A;

piposulfam;

piposulfan;

camptothecin; and ethyl-3,5-diacetoamido-2,4,6-triiodobenzoate

The described block copolymer surface modifiers can be used with NSAIDS. Surface modified nanoparticles comprising an NSAID, e.g., naproxen, demonstrate reduced gastric irritation and/or a more rapid onset of action following oral administration.

Useful NSAIDs can be selected from suitable acidic and nonacidic compounds. Suitable acidic compounds include carboxylic acids and enolic acids. Suitable nonacidic compounds include, for example, nabumetone, tiaramide, proquazone, bufexamac, flumizole, epirazole, tinoridine, timegadine and dapsone.

Suitable carboxylic acid NSAIDs include, for example, salicylic acids and esters thereof, such as aspirin, diflunisal, benorylate and fosfosal; acetic acids, including phenylacetic acids such as diclofenac, alclofenac and fenclofenac, and carbo- and heterocyclic acetic acids such as etodolac, indomethacin, sulindac, tolmetin, fentiazac and tilomisole; propionic acids, such as carprofen, fenbufen, flurbiprofen, ketoprofen, oxaprozin, suprofen, tiaprofenic acid, ibuprofen, naproxen, fenoprofen, indoprofen, pirprofen; and fenamic acids, such as flufenamic, mefenamic, meclofenamic and niflumic.

Suitable enolic acid NSAIDs include, for example, pyrazolones such as oxyphenbutazone, phenylbutazone, apazone and feprazone, and oxicams such as piroxicam, sudoxicam, isoxicam and tenoxicam.

Preferred diagnostic agents include the x-ray imaging agent WIN-8883 (ethyl 3,5-diacetamido-2,4,6-triiodobenzoate) also known as the ethyl ester of diatrazoic acid (EEDA), WIN 67722, i.e., (6-ethoxy-6-oxohexyl- 3,5-bis(acetamido)-2,4,6-triiodobenzoate; ethyl-2-(3,5-bis(acetamido)-2,4,6-triiodobenzoyloxy)butyrate (WIN 16318); ethyl diatrizoxyacetate (WIN 12901); ethyl 2-(3,5-bis(acetamido)- 2,4,6-triiodobenzoyloxy)propionate (WIN 16923); N-ethyl 2-(3,5-bis(acetamido)-2,4,6-triiodobenzoyloxy acetamide (WIN 65312); isopropyl 2-( 3,5-bis(acetamido)-2,4,6-triiodobenzoyloxy) acetamide (WIN 12855); diethyl 2-(3,5-bis(acetamido)-2,4,6-triiodobenzoyloxy malonate (WIN 67721); and ethyl 2-( 3,5-bis(acetamido)-2,4,6-triiodobenzoyloxy) phenylacetate (WIN 67585). Suitable diagnostic agents are also disclosed in U.S. Pat. No. 5,260,478; U.S. Pat. No. 5,264,610; U.S. Pat. No. 5,322,679 and U.S. Pat. No. 5,300,739.

The present surface modifiers are particularly useful with diagnostic imaging agents because they provide excellent bioadhesive effect in the GI tract. The increase in viscosity and gelation in the GI tract provides good even coating of the diagnostic agent on the wall of the tract and thus provides an excellent imaging effect which last for more than 24 hours.

Grinding

The described particles can be prepared in a method comprising the steps of dispersing a therapeutic or diagnostic agent in a liquid dispersion medium and applying mechanical means in the presence of grinding media to reduce the particle size of the therapeutic or diagnostic agent to an effective average particle size of less than about 400 nm. The particles can be reduced in size in the presence of a surface modifier. Alternatively, the particles can be contacted with a surface modifier after attrition.

The therapeutic or diagnostic agent selected is obtained commercially and/or prepared by techniques known in the art in a conventional coarse form. It is preferred, but not essential, that the particle size of the coarse therapeutic or diagnostic agent selected be less than about 100 µm as determined by sieve analysis. If the coarse particle size of the therapeutic or diagnostic agent is greater than about 100 µm, then it is preferred that the particles of the therapeutic or diagnostic agent be reduced in size to less than 100 µm using a conventional milling method such as airier or fragmentation milling.

The coarse therapeutic or diagnostic agent selected can then be added to a liquid medium in which it is essentially insoluble to form a premix. The concentration of the therapeutic or diagnostic agent in the liquid medium can vary from about 0.1–60%, and preferably is from 5–30% (w/w). It is preferred, but not essential, that the surface modifier be present in the premix. The concentration of the surface modifier can vary from about 0.1 to about 90%, and preferably is 1–75%, more preferably 20–60%, by weight based on the total combined weight of the therapeutic or diagnostic agent and surface modifier. The apparent viscosity of the premix suspension is preferably less than about 1000 centipoise The premix can be used directly by subjecting it to mechanical means to reduce the average particle size in the dispersion to less than 400 nm. It is preferred that the premix be used directly when a ball mill is used for attrition. Alternatively, the therapeutic or diagnostic agent and, optionally, the surface modifier, can be dispersed in the liquid medium using suitable agitation, e.g., a roller mill or a Cowles type mixer, until a homogeneous dispersion is observed in which there are no large agglomerates visible to the naked eye. It is preferred that the premix be subjected to such a premilling dispersion step when a recirculating media mill is used for attrition.

The mechanical means applied to reduce the particle size of the therapeutic or diagnostic agent conveniently can take the form of a dispersion mill. Suitable dispersion mills include a ball mill, an attritor mill, a vibratory mill, and media mills such as a sand mill and a bead mill. A media mill is preferred due to the relatively shorter milling time required to provide the intended result, i.e., the desired reduction in particle size. For media milling, the apparent viscosity of the premix preferably is from about 100 to about 1000 centipoise. For ball milling, the apparent viscosity of the premix preferably is from about 1 up to about 100 centipoise. Such ranges tend to afford an optimal balance between efficient particle fragmentation and media erosion.

Preparation Conditions

The attrition time can vary widely and depends primarily upon the particular mechanical means and processing conditions selected. For ball mills, processing times of up to five days or longer may be required. On the other hand, processing times of less than 1 day (residence times of one minute up to several hours) have provided the desired results using a high shear media mill.

The particles must be reduced in size at a temperature which does not significantly degrade the therapeutic or diagnostic agent. Processing temperatures of less than about 25°–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Control of the temperature, e.g., by jacketing or immersion of the milling chamber in ice water are contemplated. Processing pressures from about 1 psi (0.07 kg/cm$^2$) up to about 50 psi (3.5 kg/cm$^2$) are contemplated. Processing pressures from about 10 psi (0.7 kg/cm$^2$) to about 20 psi (1.4 kg/cm$^2$) are typical.

The surface modifier, if it was not present in the premix, must be added to the dispersion after attrition in an amount as described for the premix above. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

After attrition is completed, the grinding media is separated from the milled particulate product (in either a dry or liquid dispersion form) using conventional separation techniques, such as by filtration, sieving through a mesh screen, and the like.

Grinding Media

The grinding media for the particle size reduction step can be selected from rigid media preferably spherical or particulate in form having an average size less than about 3 mm and, more preferably, less than about 1 mm. Such media desirably can provide the particles with shorter processing times and impart less wear to the milling equipment. The selection of material for the grinding media is not believed to be critical. We have found that zirconium oxide, such as 95% ZrO stabilized with magnesia, zirconium silicate, and glass grinding media provide particles having levels of contamination which are believed to be acceptable for the preparation of pharmaceutical compositions. However, other media, such as stainless steel, titania, alumina, and 95% ZrO stabilized with yttrium, are expected to be useful. Preferred media have a density greater than about 3 g/cm$^3$.

Polymeric Grinding Media

The grinding media can comprise particles, preferably substantially spherical in shape, e.g., beads, consisting essentially of polymeric resin. Alternatively, the grinding media can comprise particles comprising a core having a coating of the polymeric resin adhered thereon.

In general, polymeric resins suitable for use herein are chemically and physically inert, substantially free of metals, solvent and monomers, and of sufficient hardness and friability to enable them to avoid being chipped or crushed during grinding. Suitable polymeric resins include crosslinked polystyrenes, such as polystyrene crosslinked with divinylbenzene, styrene copolymers, polycarbonates, polyacetals, such as Delrin™, vinyl chloride polymers and copolymers, polyurethanes, polyamides, poly(tetrafluoroethylenes), e.g., Teflon™, and other fluoropolymers, high density polyethylenes, polypropylenes, cellulose ethers and esters such as cellulose acetate, polyhydroxymethacrylate, polyhydroxyethyl acrylate, silicone containing polymers such as polysiloxanes and the like. The polymer can be biodegradable. Exemplary biodegradable polymers include poly(lactides), poly(glycolide) copolymers of lactides and glycolide, polyanhydrides, poly(hydroxyethyl methacylate), poly(imino carbonates), poly(N-acylhydroxyproline)esters, poly(N-palmitoyl hydroxyproline) esters, ethylene-vinyl acetate copolymers, poly(orthoesters), poly(caprolactones), and poly(phosphazenes). In the case of biodegradable polymers, contamination from the media itself advantageously can metabolize in vivo into biologically acceptable products which can be eliminated from the body.

The polymeric resin can have a density from 0.8 to 3.0 g/cm$^3$. Higher density resins are preferred inasmuch as it is believed that these provide more efficient particle size reduction.

The media can range in size from about 0.1 to 3 mm. For fine grinding, the particles preferably are from 0.2 to 2 mm, more preferably, 0.25 to 1 mm in size.

In a particularly preferred method, a therapeutic or diagnostic agent is prepared in the form of submicron particles by grinding the agent in the presence of a grinding media having a mean particle size of less than about 75 microns.

The core material of the grinding media preferably can be selected from materials known to be useful as grinding media when fabricated as spheres or particles. Suitable core materials include zirconium oxides (such as 95% zirconium oxide stabilized with magnesia or yttrium), zirconium silicate, glass, stainless steel, titania, alumina, ferrite and the like. Preferred core materials have a density greater than about 2.5 g/cm$^3$. The selection of high density core materials is believed to facilitate efficient particle size reduction.

Useful thicknesses of the polymer coating on the core are believed to range from about 1 to about 500 microns, although other thicknesses outside this range may be useful in some applications. The thickness of the polymer coating preferably is less than the diameter of the core.

The cores can be coated with the polymeric resin by techniques known in the art. Suitable techniques include spray coating, fluidized bed coating, and melt coating. Adhesion promoting or tie layers can optionally be provided to improve the adhesion between the core material and the resin coating. The adhesion of the polymer coating to the core material can be enhanced by treating the core material to adhesion promoting procedures, such as roughening of the core surface, corona discharge treatment, and the like.

Continuous Grinding

In a preferred grinding process, the particles are made continuously rather than in a batch mode. The continuous method comprises the steps of continuously introducing the therapeutic or diagnostic agent and rigid grinding media into a milling chamber, contacting the agent with the grinding media while in the chamber to reduce the particle size of the agent, continuously removing the agent and the grinding media from the milling chamber, and thereafter separating the agent from the grinding media.

The therapeutic or diagnostic agent and the grinding media are continuously removed from the milling chamber. Thereafter, the grinding media is separated from the milled particulate agent (in either a dry or liquid dispersion form) using conventional separation techniques, in a secondary process such as by simple filtration, sieving through a mesh filter or screen, and the like. Other separation techniques such as centrifugation may also be employed.

In a preferred embodiment, the agent and grinding media are recirculated through the milling chamber. Examples of suitable means to effect such recirculation include conventional pumps such as peristaltic pumps, diaphragm pumps, piston pumps, centrifugal pumps and other positive displacement pumps which do not use sufficiently close tolerances to damage the grinding media. Peristaltic pumps are generally preferred.

Another variation of the continuous process includes the use of mixed media sizes. For example, larger media may be employed in a conventional manner where such media is restricted to the milling chamber. Smaller grinding media may be continuously recirculated through the system and permitted to pass through the agitated bed of larger grinding media. In this embodiment, the smaller media is preferably between about 1 and 300 mm in mean particle size and the larger grinding media is between about 300 and 1000 mm in mean particle size.

Precipitation Method

Another method of forming the deisred nanoparticle dispersion is by microprecipitation. This is a method of preparing stable dispersions of therapeutic and diagnostic agents in the presence of a surface modifying and colloid stability enhancing surface active agent free of trace of any toxic solvents or solubilized heavy metal inpurities by the following procedural steps:

1. Dissolving the therapeitic or diagnostic agent in aqueous base with stirring,
2. Adding above #1 formulation with stirring to a surface active surfactant (or surface modifiers) solution to form a clear solution, and,
3. Neutralizing above formulation #2 with stirring with an appropriate acid solution. The procedure can be followed by:
4. Removal of formed salt by dialysis or diafiltration and
5. Concentration of dispersion by conventional means.

This microprecipitation process produces dispersion of therapeutic or diagnostic agents with Z-average particle diameter less than 400 nm (as measured by photon correlation spectroscopy) that are stable in particle size upon keeping under room temperature or refrigerated conditions. Such dispersions also demonstrate limited particle size growth upon autoclave-decontamination conditions used for standard blood-pool pharmaceutical agents.

Step 3 can be carried out in semicontinuous, continuous batch, or continuous methods at constant flow rates of the reacting components in computer-controlled reactors or in tubular reactors where reaction pH can be kept constant using pH-stat systems. Advantages of such modifications are that they provide cheaper manufacturing procedures for large-scale production of nanoparticulate dispersion systems.

Additional surface modifier may be added to the dispersion after precipitation. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

In a preferred embodiment, the above procedure is followed with step 4 which comprises removing the formed salts by diafiltration or dialysis. This is done in the case of dialysis by standard dialysis equipment and by diafiltration using standard diafiltration equipment known in the art. Preferably, the final step is concentration to a desired concentration of the agent dispersion. This is done either by diafiltration or evaporation using standard equipment known in this art.

An advantage of microprecipitation is that unlike milled dispersion, the final product is free of heavy metal contaminants arising from the milling media that must be removed due to their toxicity before product is formulated.

A further advantage of the microprecipitation method is that unlike solvent precipitation, the final product is free of any trace of trace solvents that may be toxic and must be removed by expensive treatments prior to final product formulation.

In another preferred embodiment of the microprecipitation process, a crystal growth modifier is used. A crystal growth modifier is defined as a compound that in the co-precipitation process incorporates into the crystal structure of the microprecipitated crystals of the pharmaceutical agent, thereby hindering growth or enlargement of the microcrystalline precipitate, by the so called Ostwald ripening process. A crystal growth modifier (or a CGM) is a chemical that is at least 75% identical in chemical structure to the pharmaceuticl agent. By "identical" is meant that the structures are identical atom for atom and their connectivity. Structural identity is characterized as having 75% of the chemical structure, on a molecular weight basis, identical to the therapeutic or diagnostic agent. The remaining 25% of the structure may be absent or replaced by different chemical structure in the CGM. The crystal growth modifier is dissolved in step #1 with the therapeutic or diagnostic agent.

Particle Size

As used herein, particle size refers to a number average particle size as measured by conventional particle size measuring techniques well known to those skilled in the art, such as sedimentation field flow fractionation, photon correlation spectroscopy, or disk centrifugation. When photon correlation spectroscopy (PCS) is used as the method of particle sizing the average particle diameter is the Z-average particle diameter known to those skilled in the art. By "an effective average particle size of less than about 400 nm" it is meant that at least 90% of the particles have a weight average particle size of less than about 400 nm when measured by the above-noted techniques. In preferred embodiments, the effective average particle size is less than about 300 nm and more preferrably less than about 250 nm. In some embodiments, an effective average particle size of less than about 100 nm has been achieved. With reference to the effective average particle size, it is preferred that at least 95% and, more preferably, at least 99% of the particles have a particle size less than the effective average, e.g., 400 nm. In particularly preferred embodiments, essentially all of the particles have a size less than 400 nm. In some embodiments, essentially all of the particles have a size less than 250 nm.

Sterilization

Sterilization can be carried out by a number of conventional methods. For example, steam or moist heat sterilization at temperatures of about 121° C. for a time period of about 15 minutes can be used. At altitudes near sea level, such conditions are attained by using steam at a pressure of 15 pounds per square inch (psi) in excess of atmospheric pressure.

Dry heat sterilization may also be performed, although the temperatures used for dry heat sterilization are typically 160° C. for time periods of 1 to 2 hours.

Sterilization can take place in the presence of cloud point modifiers such as charged phospholipids and certain nonionic or ionic compounds.

Cloud Point Modifiers

The cloud point is the temperature at which the surface modifier (surfactant) precipitates out of solution. By the phrase "cloud point modifier" is meant a compound which influences the cloud point of surface modifiers. In particular, the cloud point modifiers raise the cloud point of the surface modifiers in the compositions. In this way, the surface modifiers do not dissociate from the surface of the nanoparticles at temperatures used in autoclaving. Therefore, nanoparticles thus modified do not agglomerate during the sterilization process, and thus retain their effective average particle sizes of less than about 400 nm after sterilization.

Examples of cloud point modifiers include charged phospholipids. Charged phospholipids include any lipid having a net charge, i.e., any ionic phospholipid with a net positive or negative charge. Examples include such phospholipids as the synthetic phospholipid dimyristoyl phosphatidyl glycerol (DMPG), 1-palmitoyl- 2-oleoyl phosphatidyl-serine, DL-alpha-phosphatidyl-L-serine-dipalmitoyl, and cardiolipin (diphosphatidyl glycerol). Synthetic phospholipids are typically available in high purity and are relatively stable and physiologically tolerable. A preferred phospholipid is a negatively charged phospholipid. A preferred negatively charged phospholipid is dimyristoyl phosphatidyl glycerol.

The charged phospholipid can be present in an amount of 0.005–20%, preferably 0.01–15%, more preferably 0.05–10%, by weight based on the total weight of the nanoparticle suspension.

Useful Phospholipids

Useful charged phosopholipids that can be used as cluod point modifiers include:

(a) POPS: 1-Palmitoyl-2-oleoyl-phosphatidylserine (b) DPPS: Dilpalmitoylphosphatidylserine (c) DPPE: Dipalmitoylphosphatidyl-monomethylethanolamine (d) DMPG: Dimyristoylphosphatidylglycerol (e) Cardiolipin Non-ionic and Ionic Cloud Point Modifiers Sterilization can take place in the presence of non-ionic cloud point modifiers. Examples of suitable non-ionic cloud point modifiers include polyethylene glycols, e.g., PEG 300, PEG 400, PEG-1000 and PEG 2000, available from J. T. Baker Chemical Co., propylene glycol, ethanol, hydroxypropylcyclodextrin, and/or glycerol which minimize particle growth during sterilization. A preferred non-ionic cloud point modifier is PEG 400.

Sterilization can take place in the presence of ionic cloud point modifiers, such as an anionic surfactant e.g., sodium dodecyl sulfate (SDS), capronic acid, caprylic acid, dioctylsulfosuccinate (DOSS), and sodium oleate, or a cationic surfactant, such as dodecyltrimethylammonium bromide (DTAB) and tetradecyl trimethyl ammonium bromide, also known as cetrimide (TTAB), which minimize particle size growth during sterilization.

Post Sterilization Additives

The composition can be further provided with a non-ionic surfactant after sterilization (such as by autoclaving). The purpose of this additional non-ionic surfactant is to help mask the charges on the surface of the nanoparticles containing phospholipids. Masking these charges imparts longer circulation time for the nanoparticles used in intravenous applications.

Lyophilization

The compositions can be dried by the process of lyophilization. Lyophilization is the process of freeze-drying a composition to remove excess water. The process involves the sublimation of the frozen water, usually under reduced pressure conditions.

Cryoprotectants

Cryoprotectants (cryoprotective agents or compounds) are agents that protect chemical compounds, cells, or tissues from the deleterious effects of freezing that may accompany lyophilization. In the case of nanoparticles, cryoprotectants protect from the agglomeration caused by the process of lyophilization.

Exemplary cryoprotectants include carbohydrates such as the saccharide sucrose, sugar alcohols such as mannitol, surface active agents such as the Tweens™, as well as glycerol and dimethylsulfoxide. A preferred cryoprotectant is a carbohydrate. A preferred carbohydrate is a saccharide or disaccharide. A preferred disaccharide is sucrose.

Cryoprotectants can be present in an amount sufficient to allow the nanoparticles to be lyophilized. Cryoprotectants can be present in an amount of 0.5% to 90%, preferably 1–50%, and most preferably in an amount of about 2% to about 25%, based on the total weight of the nanoparticulate suspension.

The nanoparticle composition can be contacted with the cryoprotectant before lyophilization. Contacting may be by admixing a suspension of nanoparticles with a solution of cryoprotectant, followed by lyophilization at a temperature and for a time sufficient to effect freeze-drying of the nanoparticle suspension.

Dosage Forms

The resulting dispersion is stable and consists of the liquid dispersion medium and the described particles. The dispersion of surface modified therapeutic or diagnostic agent containing nanoparticles can be spray coated onto sugar spheres or onto a pharmaceutical excipient in a fluid-bed spray coater by techniques well known in the art.

Solid Forms

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes.

The active compounds can also be in micro-encapsulated form, if appropriate, with one or more of the above-mentioned excipients.

Liquid Forms

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Rectal or Vaginal Administration

Compositions for rectal or vaginal administrations are preferably suppositories which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Topical Forms

Dosage forms for topical administration of a compound include ointments, powders, sprays and inhalants. The active component is admixed under sterile conditions with a physiologically acceptable carrier and any preservatives, buffers or propellants as may be required. Ophthalmic formulations, eye ointments, powders and solutions are also contemplated as being within the scope of this invention.

Dosage Levels

Actual dosage levels of active ingredients in the compositions may be varied so as to obtain an amount of active ingredient that is effective to obtain a desired therapeutic or diagnostic response for a particular composition and method of administration. The selected dosage level therefore depends upon the desired therapeutic or diagnostic effect, on the route of administration, on the desired duration of treatment and other factors.

The total daily dose administered to a host in single or divided dose may be in amounts, for example, of from about 1 nanomol to about 5 micromoles per kilogram of body weight. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other therapeutic agents and the severity of the particular disease being treated.

Ratios

The relative amount of therapeutic or diagnostic agent and surface modifier can vary widely and the optimal amount of the surface modifier can depend, for example, upon the particular therapeutic or diagnostic agent and surface modifier selected, the critical micelle concentration of the surface modifier if it forms micelles, the hydrophilic lipophilic balance (HLB) of the stabilizer, the melting point of the stabilizer, its water solubility, the surface tension of water solutions of the stabilizer, etc. The surface modifier preferably is present in an amount of about 0.1–10 mg per square meter surface area of the therapeutic or diagnostic agent. The surface modifier can be present in an amount of 0.1–90%, preferably 20–60% by weight based on the total weight of the dry particle.

Isotonicity

Isotonicity refers to the osmotic pressure of a solution. A solution which will be administered into the blood stream of an individual is typically prepared such that the osmotic pressure of that solution is the same as the osmotic pressure of blood. Such a solution is said to be isotonic.

An isotonicity maintaining compound is a compound which provides for the maintenance or alteration of a solution so as to make that solution isotonic. Such an isotonicity maintaining compound will adjust the osmotic pressure of a solution containing the compositions so as to provide, or maintain, an isotonic solution.

Exemplary isotonicity maintaining compounds include mannitol, dextrose, sodium chloride, potassium chloride, and Ringer's lactate. Preferred isotonicity maintaining compounds include mannitol and dextrose.

pH Considerations

The pH value of a solution to be delivered into the body of a subject is also an important factor. Typically, pH values should not be either too acidic or too basic. To maintain the appropriate pH value of a solution, it is preferable to provide pH value maintaining compounds. These compounds provide a buffering capacity to the solution, to prevent extremes of pH values of the solution upon storage or upon subsequent manipulation.

Exemplary pH value maintaining compounds include the well known buffers such as Tris base, HEPES, carbonate, phosphate, citrate and acetate salts. A preferred buffer is sodium phosphate (either mono- or di-basic, or both).

Additives

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Method of Treating

A method of treating or diagnosing a mammal comprises the step of administering to the mammal in need of treatment an effective amount of the above-described therapeutic or diagnostic agent composition. The selected dosage level of the therapeutic or diagnostic agent for treatment is effective to obtain a desired therapeutic or diagnostic response for a particular composition and method of administration. The selected dosage level therefore, depends upon the particular therapeutic or diagnostic agent, the desired therapeutic or diagnostic effect, on the route of administration, on the desired duration of treatment and other factors.

It is contemplated that the therapeutic or diagnostic compositions will be particularly useful in oral, subcutaneous, topical and nasasl administration applications. It is expected that poorly water soluble therapeutic or diagnostic agents, which prior to this invention, could not have been administered subcutaneously, may be administered safely. Additionally, therapeutic or diagnostic agents which could not have been administered orally due to poor bioavailability may now be effectively administered. Diagnosis A method for diagnostic imaging for use in medical procedures in accordance with this invention comprises administering to the body of a test subject in need of a diagnostic image an effective contrast producing amount of the diagnostic image contrast composition. In addition to human patients, the test subject can include mammalian species such as rabbits, dogs, cats, monkeys, sheep, pigs, horses, bovine animals and the like. Thereafter, at least a portion Of the body containing the administered contrast agent is exposed to x-rays or a magnetic field to produce an x-ray or magnetic resonance image pattern corresponding to the presence of the contrast agent. The image pattern can then be visualized.

Any x-ray visualization technique, preferably, a high contrast technique such as computed tomography, can be applied in a conventional manner. Alternatively, the image pattern can be observed directly on an x-ray sensitive phosphor screen-silver halide photographic film combination or by use of a storage phosphor screeen.

Visualization with a magnetic resonance imaging system can be accomplished with commercially available magnetic imaging systems such as a General Electric 1.5 T Sigma imaging system [1H resonant frequency 63.9 megahertz (MHz)]. Commercially available magnetic resonance imaging systems are typically characterized by the magnetic field strength used, with a field strength of 2.0 Tesla as the current maximum and 0.2 Tesla as the current minimum. For a given field strength, each detected nucleus has a characteristic frequency. For example, at a field strength of 1.0 Tesla, the resonance frequency for hydrogen is 42.57 MHz; for phosphorus-31 it is 17.24 MHz; and for sodium- 23 it is 11.26 MHz.

A contrast effective amount of the diagnostic agent containing composition is that amount necessary to provide tissue visualization with, for example, magnetic resonance imaging or x-ray imaging. Means for determining a contrast effective amount in a particular subject will depend, as is well known in the art, on the nature of the magnetically reactive material used, the mass of the subject being imaged, the sensitivity of the magnetic resonance or x-ray imaging system and the like.

After administration of the compositions, the subject mammal is maintained for a time period sufficient for the administered compositions to be distributed throughout the subject and enter the tissues of the mammal. Typically, a sufficient time period is from about 20 minutes to about 90 minutes and, preferably from about 20 minutes to about 60 minutes.

The folowing Preparation illustrates the preparation of a block polymer that is useful in the present invention.

Preparation

An oxymethylene linked, multiblock copolymer was prepared by the reaction of an $E_{141}P_{44}E_{141}$ triblock copolymer of poly(oxyethylene) ($E_{141}$) and poly(oxypropylene) ($P_{44}$), having an average molecular weight of 14,500, (Pluronic™ 108) with dichloromethane in the presence of potassium hydroxide.

Finely ground potassium hydroxide (66 g) was mixed with dichloromethane (300 mL) under a nitrogen atmosphere at room temperature in a one liter resin kettle equipped with a condenser and a mechanical stirrer. To this was added the triblock copolymer (100 g) dispersed in dichloromethane (700 mL).

The whole was stirred for approximately two hours, then additional dichloromethane (500 mL) was added to reduce the viscosity of the polymer solution. The solution was filtered through a pad of Celite™ (Kieselguhr) and then rotary evaporated under vacuum to give a polymer.

The polymer was characterised by gel permeation chromatography (GPC). Dimethyl formamide (DMF) eluant and styragel columns were employed, calibrated with poly(oxyethylene) standards. Molecular weights and molecular weight distributions were obtained from the GPC curve by reference to this calibration. The preparation was repeated three times with average molecular weights ranging 50,824 to 68,092. The gel point at 4% concentration ranged from 33° to 36° C.

Second Preparation

Pluronic™ F108, as used in the first preparation, and polyethylene glycol (50 g) were dissolved in dichloromethane and added rapidly to a stirred suspension of powdered sodium hydroxide (100 g) in dichloromethane (275 mL) and stirred under nitrogne for 15–18 hours. The mixture was diluted with dichloromethane (1200 mL), allowed to settle and filtered through a Celite pad to remove inorganics. The solvent was then evaporated.

The product polymer has an average molecular weight of 89,267 and a gel point of 46° C. (4% concentration in deionized water.

EXAMPLES 1 and 2

Preparation of Nanoparticles with Diagnostic Agent for Oral Imaging in Rats

The following formulations were prepared at 20% (EEDA) and 4% surfactant (w/v). A 6% stock solution was prepared by dissolving 600 mL of the surface modifier prepared in the first preparation (hereinafter SM108) or 600 mL of the surface modifier prepared according to the second preparation (hereinafter SM108/6000) in 10 mL deionized water.

To each of two 20 mL bottles, 10 mL $ZrSiO_4$ beads of size 1.1 mm, 1 g of EEDA, 4 mL of 6% stock solution and 1.26 mL deionized water was added. The sample bottles were sealed and placed in a planetary mill running at 165 rpm for 3 days with the temperature kept below 30 degrees C. At day 3, an aloquot of each sample was diluted 300 fold with deionized water for particle size measurement by PCS.

The SM108 nanoparticles had a mean particle size of 230 nm; the SM108/6000 nanoparticles had a mean particle size of 312 nm.

This data demonstrates that the polyalkylene block copolymers were able to effectively reduce the mean particle size of the contrat agent to less than 400 nm. Evaluation of the temperature effec on these two formulation wiry a digital rotary viscometer revealed abrupt change of viscosity at temperatures between 30° to 37° C. (from less than 20 cps to greater than 1000 cps) as a result of gello formation.

This change in viscoelasticity because of the increased area of hydrophobic region in SM108 and SM108/6000 resulted in excellent GI images which lasted for more than 24 hours as indicated by repeated X-ray flat film imaging using a Siemans X-ray machine after oral intubation of 10 mL/kg formulations and 10 mL of air to anathezized rats.

The invention has been described with particular reference to preferred embodiments thereof, but it will be understood that variations and modifications can be effected within the spirit and scope of the invention.

We claim:

1. A composition comprised of nanoparticles comprising a therapeutic or diagnostic agent having a surface modifier adsorbed on the surface thereof, the improvement wherein the surface modifier is a triblock copolymer having the following repeating units in random order $$-((E_rP_sE_r)CH_2O)_z-$$

wherein

P is oxypropylene;

E is oxyethylene;

r is an integer from 2 to 160;

s is an integer from 15 to 65; and z is an integer from 2 to 50 and wherein the triblock copolymer gels at physiological temperature.

2. A composition according to claim 1 wherein said block copolymer has the formula:

$$-[(CH_2CH_2O)_r(CH_2\underset{\underset{CH_3}{|}}{C}HO)_s(CH_2CH_2O)_r(CH_2O)]_z-$$

wherein r is 141; s is 44 and z is 3 to 4.

3. A composition according to claim 1 wherein said therapeutic agent is an agent for treating glaucoma.

4. A composition according to claim 3 wherein said therapeutic agent is (S)-1-[(1,1-dimethyl-ethyl)amino]- 3-[[4-(4-morpholinyl)-1,2,5-thiadiazol-3-yl-oxy]-2-propanol (Z)butenedioate (1:1) salt.

5. A composition according to claim 1 wherein said diagnostic agent is a radiographic contrast agent.

6. A composition according to claim 5 wherein said contrast agent is (ethyl 3,5-diacetamido-2,4,6-triiodobenzoate).

* * * * *